May 15, 1934. J. D. BROWNELL Plant Pat. 96
ROSE PLANT
Filed May 19, 1933
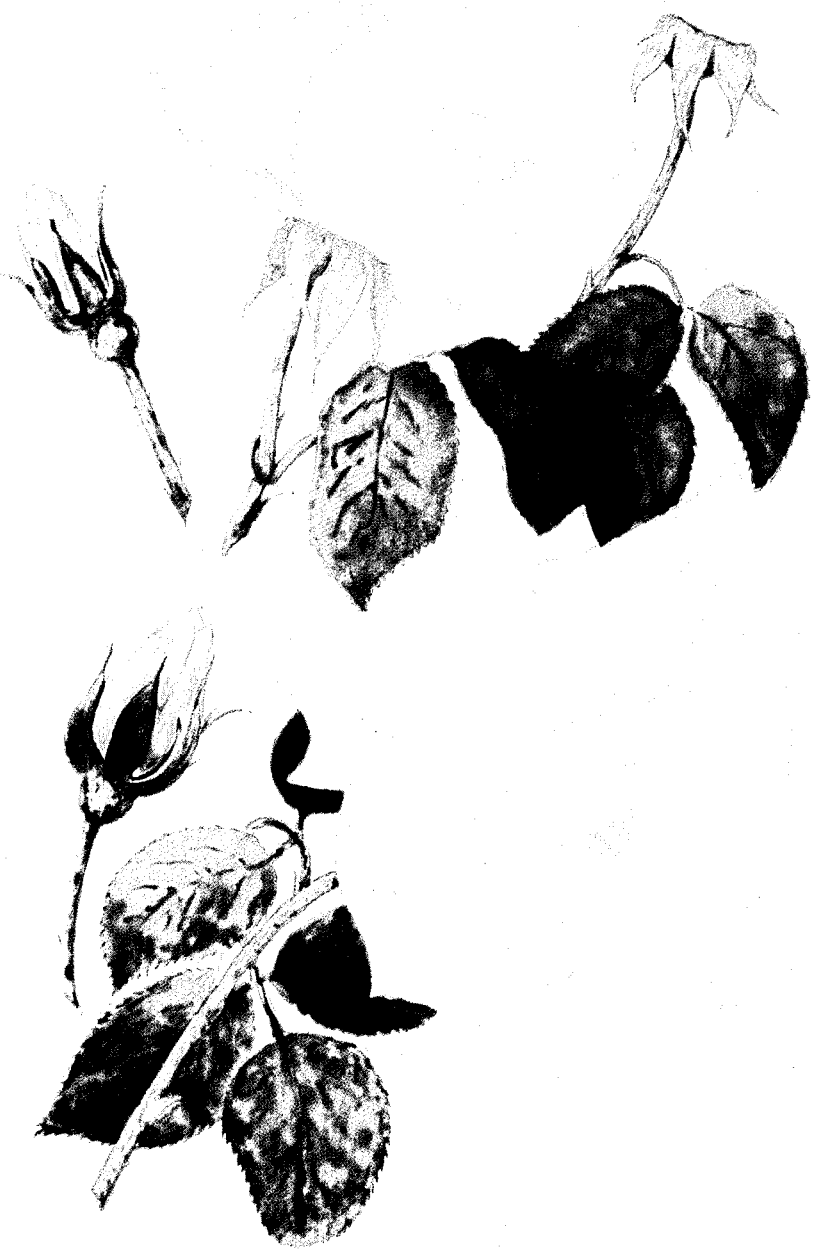
INVENTOR
Josephine D. Brownell Patented May 15, 1934

Plant Pat. 96

UNITED STATES PATENT OFFICE

96

ROSE PLANT

Josephine D. Brownell, Little Compton, R. I.

Application May 19, 1933, Serial No. 671,871

1 Claim. (Cl. 47—61)

My invention relates to roses and especially to a new, original and distinct variety of the class known commercially as "hardy climbing roses", produced by propagation and by bud sport or mutation and that said sport or mutation occurred in a plant of the variety designated as 2305 the subject of Plant Patent 28, asexually reproduced.

My new rose is new as to the following characteristics and especially as to their joint association in connection with the characteristics of climbing and of hardiness or immunity from serious injury on account of cold temperatures prevailing in certain parts of the northern portion of the United States:—

The unique golden orange of its petals and their tendency to hold their orange color under exposure; this color has been described by leading rosarians as orange scarlet to orange carmine, and is closely comparable with the colors orange to "copper" to "chamois" as classified by the Gravereaux system, and to cadmium orange of the artist's pallet;

The novelty and variation within certain definite limits of the form of the bloom and its large size;

Its special cut flower value due to its unusually long stem in a hardy climbing rose and its tendency to produce a very limited number of blooms on each stem, frequently but one;

Its intensity and character of fragrance, and

Its remontant and everblooming habit.

In the accompanying drawing forming a part of this specification I have shown my new rose in its natural colors, that is, as near as is possible to do so artificially.

I otherwise describe my new rose as follows:

My new rose is a hardy hybrid Rosa Wichuraiana, a variation or bud sport or mutation in or of a rose plant crossed in its ancestral generations with, in addition to Rosa Wichuraiana, several so-called hybrid tea and species roses.

The characteristics of my new rose are except as to bud and bloom and blooming characters and except as herein described, substantially similar to the hardy climbing roses known commercially as "Mary Wallace" and as "Golden Climber Mrs. Arthur Curtiss James" (Plant Patent 28) or more like said roses than any other roses. My new rose is otherwise described as follows.

Bloom period under comparable conditions begins about three days after the bloom period of "Mary Wallace" begins, attains maximum intensity of bloom about two weeks thereafter then diminishes in intensity of bloom and is everblooming and intermittently remontant until winter dormancy.

*Bud*

Size:—Large, usually 1½ to 2 inches in length. Shape:—Long, pointed to tapering. Color:—Orange scarlet to orange carmine to copper to chamois, self; variable in intensity, usually of intense brilliance.

*Flower*

First stages of opening, high centered. Tea to hybrid tea type. Size open usually 4 to 5 inches, often larger.

Petals variable in number usually three to four rows with an inner row of petaloids.

Number averaging around twenty.

Petaloids vary around four.

Petals unfurl from flat to cupped to curled and often wrinkled, with edges plain to irregular to indented to scalloped; semi-double.

Bloom retains an unique informal to artistic character; very good lasting quality.

Fragrance, blended, pleasant to sweet, medium to strong. Rosa Wichuraiana and China Tea in part.

Color, golden orange to orange scarlet, to orange carmine to "copper" to "chamois", self; variable in intensity, often with a reflex of golden yellow. It is particularly noticeable on account of its tendency to retain its color under test of exposure better than many orange roses; it however fades and more rapidly so in the sun to sulphur to "Maréchal Niel yellow" overlaid with orange to lighter orange. The orange tones often appear in intensity in a stippled or splashed manner.

Petals fall. Calyx clings.

Borne on stiff stems usually one to two feet long, often longer. Noticeable for its limited number of blooms on stem, very frequently but one bloom on each stem.

*Thorns and prickles*

New growth nearly blood red to nearly vermillion, fading to a dull weather color.

*Vigor*

Very vigorous.

*Form*

Climbing, branching.

My new rose is hardy and resistant to normal winter temperatures and conditions in certain parts of the Northern United States and capable of surviving such winter conditions without serious injury.

Foliage is normal, normal green, glossy texture, medium size. Bark is green. The plant is resistant to disease.

I claim:—

A hardy climbing rose plant as disclosed, characterized by its remontant and everblooming habit, stiff long stems, limited number of blooms per bloom stem, the flower having large size and intense fragrance with form and color substantially as shown, being substantially a self flower with petals of a unique golden orange color but variable in different specimens to orange scarlet to orange carmine, to copper to chamois, or to cadmium orange, often overlaid with golden yellow.

JOSEPHINE D. BROWNELL.